United States Patent [19]
Gruter et al.

[11] Patent Number: 6,063,948
[45] Date of Patent: *May 16, 2000

[54] PROCESS FOR CYCLOPENTADIENE SUBSTITUTION WITH GROUPS DIFFERING FROM EACH OTHER

[75] Inventors: Gerardus J. M. Gruter, Maastricht, Netherlands; Johannes A. M. van Beek, Mountain View, Calif.; Richard Green, Geleen, Netherlands

[73] Assignee: DSM N.V., Heerlen, Netherlands

[ * ] Notice: This patent is subject to a terminal disclaimer.

[21] Appl. No.: 09/184,064

[22] Filed: Nov. 2, 1998

Related U.S. Application Data

[63] Continuation of application No. PCT/NL97/00211, Apr. 23, 1997.

[30] Foreign Application Priority Data

May 3, 1996 [NL] Netherlands .......................... 1003004

[51] Int. Cl.[7] ................................ C07F 17/00; C08F 4/64

[52] U.S. Cl. ................................ 556/11; 556/43; 556/53; 585/375; 526/126; 526/160; 526/943; 526/161; 987/2

[58] Field of Search .................................. 556/11, 43, 53; 585/375; 526/126, 160, 943, 161; 987/2

[56] References Cited

U.S. PATENT DOCUMENTS

| | | | |
|---|---|---|---|
| 2,916,503 | 12/1959 | Kozikowski | ............................ 260/429 |
| 5,563,284 | 10/1996 | Frey et al. | ................................ 556/53 |

FOREIGN PATENT DOCUMENTS

| | | |
|---|---|---|
| 0 416 815 A2 | 3/1991 | European Pat. Off. . |
| 0 728 724 | 8/1996 | European Pat. Off. . |
| 0 728 769 A1 | 8/1996 | European Pat. Off. . |
| 0 728 770 A1 | 8/1996 | European Pat. Off. . |
| 43 03 647 | 8/1994 | Germany . |
| 864198 | 3/1961 | United Kingdom . |
| WO 95/00562A | 1/1995 | WIPO . |
| WO 96/13529 | 5/1996 | WIPO . |

OTHER PUBLICATIONS

Szymoniak et al., "New Heterodifunctional Ligands for Organotransiton–Metal Chemistry . . . ", Journal of Organic Chemistry, 1990, vol. 55, pp. 1429–1432.

Ying Mu et al., "Use of Alkane Elimination in the One–step Synthesis of Organoscandium Complexes Containing a New Multidentate Cyclopentadienyl Ligand", Organometallics, 1996, vol. 15, pp. 2720–2726.

Chemical Abstracts, vol. 123, No. 13 (Sep. 1995), Abstract No. 169881g.

Weinheim DE, K. Hafner et al., "Synthesen und Reaktionen von Fulvenaldehyden", Chemische Berichte, 1963, vol. 661, pp. 52–75.

G. Kresze et al., "Substitierte Cyclopentadiene und ihre Diels–Alder–Reaktionen", Chemische Berichte, 1963, vol. 666, pp. 45–53.

Krut'ko, D.P. et al., "Tetramethyl(2–methyl- thioethyl)cyclopentadienyl Complexes of Zirconium(IV): Synthesis, . . . Solutions", Russian Chemical Bulletin, 1996, vol. 45, No. 4, pp. 940–949.

Ulrich Siemeling, "$C_5Me_4(CH_2)_3OMe$: A Tentacle–bearing Cyclopentadienyl Ligand and Its Use in Complex Chemistry", J. Chem. Soc. Commun., 1992, vol. 18, pp. 1335–1336.

R. Allen Williams et al., 'Encapsulated Alkaline–Earth Metallocenes. Synthesis, Solution Behavior, and Solid–State Structures of . . . ', Journal of the American Chemical Society, vol. 113, No. 13, Jun. 19, 1991, pp. 4843–4851.

Clifford G. Venier et al., 'D–tert–butylcyclopentadiene and Tri–tert–butylcyclopentadiene', Journal of the American Chemical Society, vol. 112, No. 7, Mar. 28, 1990.

Eckehard V. Dehmlow et al., 'Phase Transfer Catalyzed tert–Alkylations of Cyclopentadiene and Indene: Indications for Set Processess', Tetrahedron Letters, vol. 32, No. 41, Oct. 1991.

R.H. Chung, et al., "1–Isopropyl–4–methylenebicyclo [3.1.0]hex–2–ene. Synthesis and reactions", J. Amer. Chem. Soc., vol. 94(7), pp. 2183–2187, 1972.

G. Moran et al., "Formation of a fulvene by trimerisation of an alkyne at a Rhodium centre; . . . ", Journal of Organometallic Chemistry, vol. 250, 1983, pp. C15–C20.

T. Jeffrey Clark et al., "Regioselective synthesis of dialkyl–1,3–cyclopentadienes via novel 2–alkyl–6,6–dialkylfulvenes" Synlett (1990), (10), 589–90.

T. Leigh, "Ferrocene Derivatives containing Tertiary Alkyl Groups. Synthesis by the Friedel–Crafts and Other Methods", Journal of the Chemical Society, 1964, Letchworth GB, pp. 3294–3302.

R.R. Schrock et al., "Formation of Cyclopentadienyl Complexes from Tungstenacyclobutadiene Complexes and the X–ray Crystal Structure of an eta–3–Cyclopropenyl Complex, W[C(CMe3)C(Me)C(Me)](Me2NCH2CH2NMe2) Cl3", Organometallics, vol. 3, No. 10, 1984, pp. 1574–1583.

H. Van Der Heijden et al., "Reactions of the Trimetallic Neopentylidene Complex [{Cl2(MeOCH2CH20Me)Ta (mu–CCMe3)}2Zn(mu–Cl)2] with Alkynes. A Structural Study of [(eta5–C5(t–Bu)(CH2CMe3)2(CH2CME2CH2)2) TaCl2]", Organometallics, vol. 4, No. 10, 1985, pp. 1847–1853.

(List continued on next page.)

*Primary Examiner*—Porfirio Nazario-Gonzalez
*Attorney, Agent, or Firm*—Intellectual Property Group Pillsbury Madison & Sutro LLP

[57] ABSTRACT

Polysubstituted cyclopentadiene compound wherein at least two different substituents are present from the group consisting of linear, branched and cyclic alkyls, aralkyls and alkenyls, and a process for the preparation of a cyclopentadiene compound substituted with at least two different groups chosen from the group consisting of linear, branched, cyclic and aromatic alkyls and alkenyls, characterized in that it comprises the reacting of a halide of a first substituting group in a mixture of the cyclopentadiene compound and an aqueous solution of a base, in which the quantity of the base relative to the cyclopentadiene compound is between 5 and 30 mol/mol, in the presence of a phase transfer catalyst, followed by the addition of a halide of a second or optionally a third substituting group to the reaction mixture.

14 Claims, No Drawings

OTHER PUBLICATIONS

Sappa Enrico et al., "Mass spectral investigations on sigma–pi bonded binuclear alkyne–carbonyl derivatives of iron. Fe2(CO)5/C2RR')3(C)) and Fe2(CO)6/C2RR')3 complexes", Chemical Abstracts, vol. 91, No. 9 (Aug. 27, 1979, Abstract No. 73791x.

Bensley, Jr. et al.; "Synthesis of $[C_5(CH_3)_4H]CH_2CH_2ch_2P(C^6H_5)_2$: A Novel . . . Functionality"; J. Org. Chem. 1988, vol. 53, pp. 4417–19.

Balakrishnan, P.V. et al; (Pentamethyl–cyclopentadiene) palladium Complexes; J. Chem. Soc. (A), Inorg. Phys Theor.; 1971, pp. 1721–1725.

PROCESS FOR CYCLOPENTADIENE SUBSTITUTION WITH GROUPS DIFFERING FROM EACH OTHER

This is a Continuation of: International Appln. No. PCT/NL/97/00211 filed Apr. 23, 1997 which designated the U.S.

The invention relates to a process for the preparation of a substituted cyclopentadiene compound, which process consists of reacting a halogenide of the substituting compound in a mixture of the cyclopentadiene compound and an aqueous solution of a base in the presence of a phase transfer catalyst.

In the following the abbreviation 'Cp' will be used for cyclopentadiene. The same abbreviation will be used for a cyclopentadienyl group if it is clear from the context whether cyclopentadiene itself or its anion is meant.

Such a process is known from the Journal of the American Chemical Society, 1991, 113, 4843–4851, which describes the preparation of Cp's substituted with isopropyl groups in a mixture of aqueous KOH, isopropyl bromide and Cp in a molar ratio of 40:5:1, Adogen 464 being used as phase transfer catalyst.

A drawback of the known process is that it is not possible to obtain a cyclopentadiene compound substituted with different groups.

Another drawback of the known process is that in this case a mixture of tri- and tetraisopropyl Cp in a ratio of 65:35 is obtained, which was split up in an additional step in order to obtain the individual components in a more pure state.

The object of the invention is a process for the preparation of Cp compounds substituted with at least two different groups.

This object is achieved according to the invention in that it comprises the reacting of a halide of a first substituting compound in a mixture of the cyclopentadiene compound and an aqueous solution of a base, in which during the reaction the quantity of the base relative to the cyclopentadiene compound is at any moment between 5 and 30 mol/mol, in the presence of a phase transfer catalyst, followed by the addition of a halide of a second or optionally a further substituting compound to the reaction mixture.

A further advantage of the process according to the invention is that the substituted Cp compounds can be obtained with a great selectivity.

From J. Am. Chem. Soc., 1990, 112, 2808–2809, it is indeed known to prepare di-tert-butyl Cp with a selectivity of 90%, but such a high selectivity is an exception, as appears from the publication referred to above. It is assumed that the high selectivity in this particular case is bound up with the circumstance that a tertiary alkyl is substituted. In this case there is a high degree of steric hindrance and it is in fact the low probability of obtaining the triply substituted compound which is responsible for the high percentage of di-substituted compounds. This selection mechanism will not be effective in the case of substituents which are subject to less steric hindrance, for instance n-or sec-alkyl groups.

The two different substituting groups are chosen from the group comprising linear, branched, cyclic and aromatic alkyl, aralkyls and alkenyls.

H is not deemed to be a substituent. Besides the two required substituents the polysubstituted Cp compound can also comprise other substituents, which optionally do contain a hetero atom.

Suitable substituents, where the two differing ones as well as the optional other ones are concerned, are for instance alkyl groups, linear as well as branched and cyclic ones, alkenyl and aralkyl groups. It is also possible for these—but only where the optional other ones are concerned—to contain, apart from carbon and hydrogen, one or more hetero atoms from groups 14–17 of the Periodic System, for example O, N, Si or F, a hetero atom not being bound directly to the Cp. Examples of suitable groups are methyl, ethyl, (iso)propyl, sec-butyl, -pentyl, -hexyl and -octyl, (tert-)butyl and higher homologues, cyclohexyl, benzyl.

By Cp compounds are understood Cp as such and Cp which is already substituted in 1 to 3 positions, with the possibility of two substituents forming a closed ring. The process according to the invention thus enables unsubstituted compounds to be converted to mono- or polysubstituted ones, but also already mono- or polysubstituted Cp-based compounds to be substituted further, which can also be followed by ring closure.

The process according to the invention is preferably carried out with a virtually equivalent amount of the halogenated substituting compound in the consecutive steps. An equivalent quantity is understood as a quantity in moles which corresponds to the desired substitution multiplicity, for example 2 moles per mole of Cp compound if disubstitution with the substituent in question is intended. For the purpose of comparison, reference is made to the above-mentioned publication in the J. of Am. Chem. Soc. from 1991, where 5 equivalents of iPr-Br have to be added in order to obtain merely a mixture of three- and fourfold substituted Cp compounds. In particular if primary or secondary alkyl bromides are substituted it is preferable to use these in equivalent amounts or in an excess of at most 20%, but preferably at most 10%.

The substituting groups suitable for application in the process are as defined in the foregoing. These groups are used in the process in the form of their halides, more preferably in the form of their bromides. If bromides are used a smaller quantity of phase transfer catalyst is found to be sufficient, and a higher yield of the compound aimed for is found to be achieved.

Owing to the high degree of selectivity of the process according to the invention, it can be used to obtain, without intermediate isolation or purification, Cp compounds which are substituted with specific combinations of substituents. Thus, for example, mono- or polysubstitution with the aid of a halide of a first substituting group can first be carried out and in the same reaction mixture a subsequent mono- or polysubstitution with a halide of the second substituting group, by a second, different halide being added to the mixture after a certain time can be carried out. This can be repeated and thus the process according to the invention can also be used to prepare Cp derivatives having three or more different substituents.

The process according to the invention offers an improved selectivity relating to the substitution degree of the Cp compounds. But in some cases isomers are formed. If linear alkyls are substituted, position isomers may form as a result of competition of 1,2- and 1,3-substitution. In the case of substitution with secondary or tertiary halides of substituting compounds a second substituent will in general not be substituted in a position adjacent to the first substituent. Several double bond isomers are formed per position isomer. In the case of use as ligand in a metal complex the distinction between double bonding isomers does not play a role any more. Separation of those is therefore superfluous. The foregoing applies by analogy to triply substituted compounds. During a geminal substitution the number of substituents increases with 1, but the number of substituted carbon atoms does not increase. Geminal substitution may also occur. Geminally substituted Cp compounds can easily be separated from the non-geminally substituted ones, because the latter can be converted to a Cp-anion, in contrast to the former. All these forms of isomerism also occur in the known process, but the additional occurrence of different degrees of substitution in that process makes splitting up into the different components much more difficult than in the process according to the invention.

The substitution takes place in a mixture of the Cp compound and an aqueous solution of a base. The concentration of the base in the solution is preferably between 20 and 80 wt. %, more preferably between 40 and 60 wt. %. Concentrations of about 50 wt. % have been found to be most suitable. By preference a hydroxide of an alkali metal, for instance K or Na, is used as a base. It has been found that the use of NaOH instead of KOH which is commonly used in the state of the art results in a considerable increase in the rate of reaction, which is the reason why NaOH is preferably used as base. The base is applied in an amount of 5–30 mol per mole of Cp compound, preferably in an amount of 6–20, more preferably in an amount of 7–15 mol per mole of Cp compound. These quantities are significantly lower than the amount of 40 mol per mole of Cp compound as usual in the state of the art. It has appeared that a substantial reduction of the reaction time can be achieved if the solution of the base is refreshed during the reaction, for instance by first mixing the solution of the base with the other components of the reaction mixture and after some time isolating the aqueous phase and replacing it by a fresh portion of solution of the base. The substitution takes place at atmospheric or elevated pressure, for instance up to 100 MPa, which higher level is applied in particular if volatile components are present. The temperature at which the reaction takes place may vary within wide limits, for instance from −20 to 120° C., preferably between 10 and 50° C. Starting up the reaction at room temperature is usually suitable, after which the temperature of the reaction mixture can rise due to the heat released in the reaction.

The substitution takes place in the presence of a phase transfer catalyst which is able to transfer OH-ions from the aqueous phase to the organic phase, where they react with a H-atom which can be split off from the Cp compound. Possible phase transfer catalysts to be used are quaternary ammonium, phosphonium, arsonium, stibonium, bismuthonium, and tertiary sulphonium salts. More preferably, ammonium and phosphonium salts are used, for example tricaprylmethylammonium chloride, commercially available under the name Aliquat 336 (Fluka AG, Switzerland; General Mills Co., USA) and Adogen 464 (Aldrich Chemical Co., USA). Compounds such as benzyltriethylammonium chloride (TEBA) or benzyltriethylammonium bromide (TEBA-Br), benzyltrimethylammonium chloride, benzyltrimethylammonium bromide or benzyltrimethylammonium hydroxide (Triton B), tetra-n-butylammonium chloride, tetra-n-butylammonium bromide, tetra-n-butylammonium iodide, tetra-n-butylammonium hydrogen sulphate or tetra-n-butylammonium hydroxide and cetyltrimethylammonium bromide or cetyltrimethylammonium chloride, benzyltributyl-, tetra-n-pentyl-, tetra-n-hexyl- and trioctylpropylammonium chlorides and their bromides are likewise suitable. Usable phosphonium salts include, for example, tributylhexadecylphosphonium bromide, ethyltriphenylphosphonium bromide, tetraphenylphosphonium chloride, benzyltriphenylphosphonium iodide and tetrabutylphosphonium chloride. Crown ethers and cryptands can also be used as phase transfer catalyst, for example 15-crown-5, 18-crown-6, dibenzo-18-crown-6, dicyclohexano-18-crown-6, 4,7,13,16,21-pentaoxa-1,10-diazabicyclo[8.8.5]tricosane (Kryptofix 221), 4,7,13,18-tetraoxa-1,10-diazabicyclo[8.5.5]eicosane (Kryptofix 211) and 4,7,13,16,21,24-hexaoxa-1,10-diazabicyclo[8.8.8]-hexacosane ("[2.2.2]") and its benzo derivative Kryptofix 222 B. Polyethers such as ethers of ethylene glycols can also be used as phase transfer catalyst. Quaternary ammonium salts, phosphonium salts, phosphoric acid triamides, crown ethers, polyethers and cryptands can also be used on supports such as, for example, on a crosslinked polystyrene or another polymer. The phase transfer catalyst is used in an amount of 0.01–2, preferably 0.05–1 equivalents on the basis of the amount of Cp. compound.

The sequence of addition of the various components to the reactor as a rule is not essential in the implementation of the process. A suitable procedure is first to add solution of the base, catalyst and Cp compound and then, after thorough stirring of these, the halide of the first substituting group. It is also possible to first add and thoroughly stir the halide, the Cp compound and the catalyst and then add the solution of the base. In all the embodiments described it is found that a considerable shortening of the reaction time can be achieved if the solution of the base refreshed during the reaction, for instance by isolating the aqueous phase from the reaction mixture after some time and replacing it by a fresh portion of the solution of the base. The halide of the second substituting compound can be added simultaneously with or immediately after the addition of the fresh amount of solution of the base.

Intermediate refreshment of the solution of the base can also be done advantageously while the first halide is being reacted, the second halide being added only after some time, whether or not during or after a subsequent refreshment of the solution of the base.

The timing of replacement of the solution of the base and/or addition of any second halide of the substituting compound can be determined by monitoring the reaction in time with gas chromatography. In this relation the decrease of the rate of reaction determines the timing of replacement of the solution of the base withe gas chromatography the timing of addition of any second halide of a substituting compound can also be determined.

A further advantage of intermediate refreshing of the aqueous phase, besides the shortening of the reaction time, is that a much smaller reaction volume suffices. This advantage is achieved owing to the amount of aqueous phase as such being much smaller as well than in the process according to the state of the art.

Upon completion of the reaction the aqueous phase and the organic phase containing the Cp compound are separated. When necessary, the Cp compound is recovered by fractionated distillation.

Cp-containing compounds are for instance used as ligands in complexes of transition and other metals which are used as catalyst components, in particular in polymerization processes, more in particular α-olefin polymerization processes.

Metal complexes which are catalytically active if one of their ligands is a compound according to the invention are complexes of metals from groups 4–10 of the Periodic System and rare earths. In this context, complexes of metals from groups 4 and 5 are preferably used as a catalyst component for polymerizing olefins, complexes of metals from groups 6 and 7 in addition also for metathesis and ring-opening metathesis polymerizations, and complexes of metals from groups 8–10 for olefin copolymerizations with polar comonomers, hydrogenations and carbonylations. Particularly suitable for the polymerization of olefins are such metal complexes in which the metal is chosen from the group consisting of Ti, Zr, Hf, V and Cr.

For the Periodic System, see the new IUPAC notation to be found on the inside of the cover of the Handbook of Chemistry and Physics, 70th edition, 1989/1990.

The term olefins here and hereinafter refers to α-olefins, diolefins and other ethylenically unsaturated monomers. Where the term 'polymerization of olefins' is used, this refers both to the polymerization of a single type of olefinic monomer and to the copolymerization of two or more olefins.

Particularly suitable ligands are those in which besides the above-mentioned different groups a substituent of the form —$RDR'_n$ is present, in which R is a linking group between the Cp and the $DR'_n$ group, D is a hetero atom selected from group 15 or 16 of the Periodic System of the Elements, R' is a substituent and n is the number of R' groups bound to D. Used as ligands in metal complexes, the Cp compounds thus substituted are found to give catalysts having an enhanced activity, in particular for the polymerization of olefins, both homopolymers and copolymers, in particular if the metal in the complex is a transition metal which is not in its highest valency state. Transition metal complexes in which the metal is not in the highest valency state, but in which the Cp ligand does not comprise a group of the form $RDR'_n$, as a rule are not active at all in olefin polymerizations. In an overview article in the J. of Organomet. Chem. 479 (1994), 1–29 it is even observed that 'An important feature of these catalyst systems is that tetravalent Ti centres are required for catalytic activity'. In this context it should be kept in mind that Ti is exemplary of the metals that are suitable as metal in the commonly used cyclopentadienyl-substituted metal complexes.

The R group constitutes the bond between the Cp and the $DR'_n$ group. The length of the shortest bond between the Cp and D is critical in that, if the Cp compound is used as a ligand in a metal complex, it determines the accessibility of the metal to the $DR'_n$ group, a factor which facilitates the desired intramolecular coordination. If the R group (or bridge) is too short, the $DR'_n$ group may not be able to coordinate properly owing to ring tension. R is at least one atom long.

The R' groups can each separately be a hydrocarbon radical with 1–20 carbon atoms (such as alkyl, aryl, aralkyl, etc.). Examples of such hydrocarbon radicals are methyl, ethyl, propyl, butyl, hexyl, decyl, phenyl, benzyl and p-tolyl. R' can also be a substituent which, in addition to or instead of carbon and/or hydrogen, comprises one or more hetero atoms from groups 14–16 of the Periodic System of the Elements. Thus a substituent can be a group comprising N, O and/or Si. R' should not be a cyclopentadienyl or a cyclopentadienyl-based group.

The R group can be a hydrocarbon group with 1–20 carbon atoms (such as alkylidene, arylidene, arylalkylidene, etc.). Examples of such groups are methylene, ethylene, propylene, butylene, phenylene, with or without a substituted side chain. The R group preferably has the following structure:

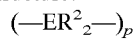

where p=1–4 and E represents an atom from group 14 of the Periodic System. The $R^2$ groups can each be H or a group as defined for R'.

Thus the main chain of the R group can also comprise silicon or germanium besides carbon. Examples of such R groups are: dialkyl silylene, dialkyl germylene, tetraalkyl disilylene or dialkyl silaethylene (—$(CH_2)(SiR^2_2)$—). The alkyl groups ($R^2$) in such a group preferably have 1 to 4 carbon atoms and more preferably are a methyl or ethyl group.

The $DR'_n$ group comprises a hetero atom D chosen from group 15 or 16 of the Periodic System of the Elements and one or more substituents R' bound to D. The number of R' groups (n) is coupled to the nature of the hetero atom D, in the sense that n=2 if D originates from group 15 and that n=1 if D originates from group 16. Preferably, the hetero atom D is chosen from the group comprising nitrogen (N), oxygen (O), phosphorus (P) or sulphur (S); more preferably, the hetero atom is nitrogen (N). The R' group is also preferably an alkyl, more preferably an n-alkyl group containing 1–20 C atoms. More preferably, the R' group is an n-alkyl containing 1–10 C atoms. Another possibility is that two R' groups in the $DR'_n$ group are joined to each other to form a ring-type structure (so that the $DR'_n$ group may be a pyrrolidinyl group). The $DR'_n$ group may bond coordinatively to a metal.

Said Cp compounds can be prepared by substituting a group of the form —$RDR'_n$ on the substituted Cp compound described above, for instance via the following synthesis route.

In a first step of this route a substituted Cp compound is deprotonated by reaction with a base, sodium or potassium.

As base can be applied for instance organolithium compounds ($R^3Li$) or organomagnesium compounds ($R^3MgX$), where $R^3$ is an alkyl, aryl, or aralkyl group and X is a halide, for instance n-butyl lithium or i-propylmagnesium chloride. Potassium hydride, sodium hydride, inorganic bases, such as NaOH and KOH, and alcoholates of Li, K and Na can also be used as base. Mixtures of the above-mentioned compounds can also be used.

This reaction can be carried out in a polar dispersing agent, for instance an ether. Examples of suitable ethers are tetrahydrofuran (THF) and dibutyl ether. Nonpolar solvents, such as for instance toluene, can also be used.

Next, in a second step of the synthesis route the cyclopentadienyl anion obtained reacts with a compound of the formula ($R'_nD-R-Y$) or (X-R-Sul), where D, R, R' and n are as defined in the foregoing. Y is a halogen atom (X) or a sulphonyl group (Sul).

The halogen atom X may be for instance chlorine, bromine and iodine. The halogen atom X preferably is a chlorine or bromine atom. The sulphonyl group has the form —$OSO_2R^6$, wherein $R^6$ is a hydrocarbon radical containing 1–20 carbon atoms, such as alkyl, aryl, aralkyl. Examples of such hydrocarbon radicals are butane, pentane, hexane, benzene and naphthalene. $R^6$ may also contain one or more hetero atoms from groups 14–17 of the Periodic System of the Elements, such as N, O, Si or F, in addition to or instead of carbon and/or hydrogen. Examples of sulphonyl groups are: phenylmethanesulphonyl, benzenesulphonyl, 1-butanesulphonyl, 2,5-dichlorobenzenesulphonyl, 5-dimethylamino-1-naphthalenesulphonyl, pentafluorobenzenesulphonyl, p-toluenesulphonyl, trichloromethanesulphonyl, trifluoromethanesulphonyl, 2,4,6-triisopropylbenzenesulphonyl, 2,4,6-trimethylbenzenesulphonyl, 2-mesitylenesulphonyl, methanesulphonyl, 4-methoxybenzenesulphonyl, 1-naphthalenesulphonyl, 2-naphthalenesulphonyl, ethanesulphonyl, 4-fluorobenzenesulphonyl and 1-hexadecanesulphonyl. Preferably, the sulphonyl group is p-toluenesulphonyl or trifluoromethanesulphonyl.

If D is a nitrogen atom and Y is a sulphonyl group, the compound according to the formula ($R'_nD-R-Y$) is formed in situ by reacting an aminoalcohol compound (R'$_2$NR—OH) consecutively with a base (such as described above), potassium or sodium and a sulphonyl halide (Sul-X).

The second reaction step can also be carried out in a polar solvent as described for the first step.

The temperature at which the reaction is carried out is −60 to 80° C. Reactions with X-R-Sul and with R'$_n$D-R-Y in which Y is Br or I are usually carried out at a temperature between −20 and 20° C. Reactions with R'$_n$D-R-Y in which Y is Cl are usually carried out at a higher temperature (10 to 80° C.). The upper limit for the temperature at which the reactions are carried out is determined in part by the boiling point of the compound R'$_n$D-R-Y and that of the solvent used.

After the reaction with a compound of the formula (X-R-Sul) another reaction is carried out with LiDR'$_n$ or HDR'$_n$ in order to replace X by a DR'$_n$ functionality. This reaction is carried out at 20 to 80° C., optionally in the same dispersant as mentioned in the foregoing.

During the synthesis process according to the invention, geminal products may in part be formed. A geminal substitution is a substitution in which the number of substituents increases by 1, but in which the number of substituted carbon atoms does not increase. The amount of geminal products formed is low if the synthesis is carried out starting from a substituted Cp compound containing 1 substituent and increases as the substituted Cp compound contains more substituents. If sterically large substituents are present on the substituted Cp compound, geminal products are not, or are scarcely, formed. Examples of sterically large substituents are secondary or tertiary alkyl substituents.

The amount of geminal product formed is also low if the second step of the reaction is carried out under the influence of a Lewis base whose conjugated acid has a dissociation constant for which $pK_a$ is less than or equal to −2.5. The $pK_a$ values are based on D. D. Perrin: Dissociation Constants of Organic Bases in Aqueous Solution, International Union of Pure and Applied Chemistry, Butterworths, London 1965. The values have been determined in an aqueous $H_2SO_4$ solution. Ethers can be mentioned as examples of suitable weak Lewis bases.

If geminal products have formed during the process according to the invention, they can easily be separated from the nongeminal products by converting the mixture of geminally and nongeminally substituted products into a salt by reaction with potassium, sodium or a base, after which the salt is washed with a dispersant in which the salt of the nongeminal products is insoluble or sparingly soluble. The compounds mentioned above may be used as base.

Suitable dispersants are nonpolar dispersants, such as alkanes. Examples of suitable alkanes are heptane and hexane.

Cp compounds thus substituted are highly suitable for use as ligands in the above mentioned metal complexes in which the metal is not in its highest valency state. Corresponding complexes in which the Cp compound is not substituted in the manner described prove unstable or, if they have been stabilized in some other way, are found to provide less active catalysts than the complexes containing substituted Cp compounds according to the invention, in particular in the case of the polymerization of α-olefins.

Moreover, the above mentioned Cp compounds in which a substituent of the form —RDR'$_n$ is present are found to be able to stabilize highly reactive intermediates such as organometal hydrides, organometal borohydrides, organometal alkyls and organometal cations. Furthermore they prove suitable as stable and volatile precursors for the use in metal chemical vapour deposition. The invention therefore also relates to a Cp compound thus substituted and to metal complexes in which such a compound is present as a ligand.

The synthesis of metal complexes with the above-described specific Cp compounds, with or without an RDR$_n$ group as a substituent, as a ligand can take place according to the methods known per se for this purpose. The use of these Cp compounds does not require any adaptations of said known methods.

The polymerization of α-olefins, for example ethene, propene, butene, hexene, octene and mixtures thereof and combinations with dienes, can be carried out in the presence of the metal complexes with the cyclopentadienyl compounds according to the invention as ligand. Suitable in particular for this purpose are the complexes of transition metals which are not in their highest valency state, in which just one of the cyclopentadienyl compounds according to the invention is present as ligand and in which the metal is cationic during the polymerization. Said polymerizations can be carried out in the manner known for the purpose and the use of the metal complexes as catalyst component does not make any essential adaptation of these processes necessary. The known polymerizations are carried out in suspension, solution, emulsion, gas phase or as bulk polymerization. The cocatalyst usually applied is an organometal compound, the metal being chosen from Groups 1, 2, 12 or 13 of the Periodic System of the Elements. To be mentioned are for instance trialkylaluminium, alkylaluminium halides, alkylaluminooxanes (such as methylaluminoxanes), tris (pentafluorophenyl) borate, dimethylanilinium tetra (pentafluorophenyl) borate or mixtures thereof. The polymerizations are carried out at temperatures between −50° C. and +350° C., more particularly between 25 and 250° C. The pressures used are generally between atmospheric pressure and 250 MPa, for bulk polymerizations more particularly between 50 and 250 MPa, and for the other polymerization processes between 0.5 and 25 MPa. As dispersants and solvents, use may be made of, for example, hydrocarbons, such as pentane, heptane and mixtures thereof. Aromatic, optionally perfluorinated hydrocarbons, are also suitable. The monomer applied in the polymerization can also be used as dispersant or solvent.

The invention will be elucidated by means of the following examples. For characterization of the Cp compounds and the synthesis results the following measurement methods were used.

Gas chromatography (GC) was performed on a Hewlett Packard 5890 Series II with an HP Crosslinked Methyl Silicon Gum (25 m×0.32 mm×1.05 μm) column. Gas chromatography combined with mass spectrometry (GC-MS) was performed with a Fisons MD800, equipped with a quadrupole mass detector, autoinjector Fisons AS800 and CPSil8 column (30 m×0.25 mm×1 μm, low bleed). NMR was performed with a Bruker ACP200 ($^1$H=200 MHz; $^{13}$C=100 50 MHz) or Bruker ARX400 NMR ($^1$H=400 MHz; $^{13}$C=100 MHz). Metal complexes were characterized using a Kratos MS80 mass spectrometer or a Finnigan Mat 4610 mass spectrometer.

EXAMPLE I a. Preparation of di(2-propyl) cyclohexylcyclopentadiene

In a double-walled reactor having a volume of 200 mL, provided with baffles, condenser, top stirrer, thermometer and dropping funnel, 150 g of clear 50% strength NaOH (1.9 mol), 7 g of Aliquat 336 (17.3 mmol) and 8.5 g (0.13 mol)

of freshly cracked cyclopentadiene were combined. The reaction mixture was stirred turbulently at a speed of 1385 rpm for a few minutes. Then 31.5 g of 2-propyl bromide (0.26 mol) were added, cooling with water taking place at the same time. Metering in took a total time of 1 hour. After addition of the bromide the reaction mixture was warmed to 50° C. After 2 hours, stirring was stopped and phase separation was awaited. The water layer was drawn off, and 150 g (1.9 mol) of fresh 50% strength NaOH were added. This was followed by the addition of 20.9 g (0.13 mol) of cyclohexyl bromide, and stirring then continued for a further 3 hours at 70° C. GC was used to show that at that instant 80% of di(2-propyl)cyclohexylcyclopentadiene were present in the mixture. The product was distilled at 0.3 mbar and 80° C. After distillation, 17.8 g of di(2-propyl)-cyclohexylcyclopentadiene were obtained. Characterization took place with the aid of GC, GC-MS, $^{13}$C- and $^{1}$H-NMR.

b. Preparation of cyclohexyl(dimethylaminoethyl)-di-(2-Propyl)cyclopentadiene

In a Schlenk vessel, to a solution of cyclohexyldiisopropylcyclopentadiene (9.28 g; 40.0 nmmol) in dry THF (150 mL) at room temperature, a solution of n-butyllithium in hexane (25.0 mL; 1.6 mol/L; 40.0 mmol) was added dropwise. Then, in another Schlenk vessel, a solution of n-butyllithium in hexane (25.0 mL; 1.6 mol/L; 40.0 mmol) was added dropwise to a cold (−78° C.) solution of dimethylaminoethanol (3.56 g; 40.0 mmol) in THF (100 mL). After an hour and a half's stirring at room temperature, the mixture was again cooled to −78° C. and the solid tosyl chloride (8.10 g; 40.0 mmol) was added slowly. The mixture was brought to 0° C., being stirred for 5 minutes in the process, again cooled to −78° C., and the mixture from the first Schlenk vessel was then added at once. After 16 hours' stirring at room temperature the conversion was 100%. After column chromatography 11.1 g of cyclohexyl-(dimethylaminoethyl)-di-(2-propyl)cyclopentadiene were obtained.

c. Synthesis of 1-(dimethylaminoethyl)-4-cyclohexyl-2,5-di(2-propyl) cyclopentadienyltitanium(III) dichloride and [1-(dimethylaminoethyl)-4-cyclohexyl-2,5-di(2-propyl) cyclopentadienyl] dimethyltitanium(III) [$C_5$H(c-Hex) (2-$C_3H_7$)$_2$($CH_2$)$_2$NMe$_2$Ti(III)Cl$_2$] and [$C_5$H(c-Hex) (2-$C_3H_7$)$_2$($CH_2$)$_2$NMe$_2$Ti(III)Me$_2$]

To lithium(dimethylaminoethyl)cyclohexyl-di(2-propyl) cyclopentadiene (2.18 g, 7.20 mmol), dissolved in 20 mL of tetrahydrofuran, a cooled slurry (−70° C.) of Ti(III)Cl$_3$. 3THF (2.67 g, 7.20 mmol) in 20 mL of THF was added at −70° C. The dark-green solution formed was stirred for 72 hours at room temperature. After this had been boiled down, 30 mL of petroleum ether (40–60) were added. After evaporating to complete dryness once more, a green powder (2.37 g) was obtained, containing 1-(dimethylaminoethyl)-4-cyclohexyl-2,5-di(2-propyl)cyclopentadienyltitanium-(III) dichloride [lithium chloride]. To a slurry, cooled to −70° C., of 0.63 g (1.36 mmol) of the [1-(dimethylaminoethyl)-4-cyclohexyl-2,5-di(2-propyl)cyclopentadienyl-titanium(III) dichloride].[lithium chloride] obtained above in 30 mL of diethyl ether, 1.70 mL of methyllithium (1.6 M in diethyl ether, 2.72 mmol) was added dropwise. The green-brown slurry immediately darkened. Then the mixture was stirred for 1 hour at room temperature, boiled down to complete dryness and dissolved in 40 mL of petroleum ether. After filtration and complete evaporation of the solvent a black powder (0.47 g, 1.22 mmol) was obtained containing 1-(dimethylaminoethyl)-4-cyclohexyl-2,5-di(2-propyl) cyclopentadienyltitanium(III)dimethyl.

We claim:

1. A process for substituting at least two different substituents onto a cyclopentadiene ring to thereby increase the number of substituents on the five-member cyclopentadiene ring, said process comprising the steps of:
   (a) reacting a compound comprising a cyclopentadiene ring with a first substituting compound comprising a halide of a first substituting group to thereby substitute the first substituting group onto the cyclopentadiene ring, said reacting step occurring in a reaction mixture comprising a phase transfer catalyst and a first aqueous phase which comprises an aqueous solution of a base in a molar ratio to the compound comprising the cyclopentadiene ring of 5 to 30 mol/mol,
   (b) reacting said cyclopentadiene ring having said first substituting group substituted thereon with a second substituting compound comprising a halide of a second substituting group to thereby substitute at least one second substituting group onto the cyclopentadiene ring to thereby obtain a substituted compound comprising a cyclopentadiene ring having said first and second substituting groups substituted thereon; and
   (c) optionally, adding a further substituent to the cyclopentadiene ring by repeating step (b) using a further substituting compound.

2. A process according to claim 1, wherein said first aqueous phase is renewed before or simultaneously with addition of the second or optional further substituting compound.

3. A process according to claim 1, wherein the amount of base relative to the cyclopentadiene compound is between 7 and 15 mol/mol.

4. A process according to claim 1, wherein said first, second and optional further substituting compounds are present in amounts, expressed in moles, equal to the desired substitution multiplicity of said first, second and optional further substituting groups, respectively.

5. A process according to claim 1, wherein said base is an alkali metal hydroxide.

6. A process according to claim 5, wherein said base is sodium hydroxide.

7. A process according to claim 1, wherein said substituting groups are selected from the group consisting of linear, branched, cyclic and aromatic alkyls, aralkyls and alkenyls.

8. A tri- or polysubstituted cyclopentadiene compound comprising a cyclopentadiene compound wherein at least one substituent is —RDR'$_n$,
   wherein R is a linking group between the cyclopentadiene compound and the DR'$_n$ group,
   D is a hetero atom selected from group 15 or 16 of the Periodic System,
   R' is a substituent on the hetero atom, each R' being independently selected from the group consisting of hydrocarbon radicals of 1 to 20 carbon atoms which may comprise one or more hetero atoms selected from groups 14, 15, or 16 of the Periodic System,
   n is the number of R' groups bonded to D, and
   the R group has a structure represented by (—ER$^2$$_2$—)$_p$,
   wherein p is an integer between 1 and 4,
   E is an element selected from group 14 of the Periodic System, and
   R$^2$ is a substituent on E, each R$^2$ being independently H or R'; and
   wherein at least two further substituents on the cyclopentadiene compound are different from one another and are independently selected from the group consisting of linear, branched and cyclic alkyls, aralkyls and alkenyls.

9. A metal complex comprising as a ligand at least one cyclopentadiene compound obtained by the process according to claim 1.

10. A metal complex comprising as a ligand at least one cyclopentadiene compound according to claim 8.

11. A metal complex according to claim 10 wherein said metal is a metal in a valency state below the metal's highest valency state.

12. A metal complex according to claim 11 wherein said metal is a metal in a valency state below the metal's highest valency state.

13. A process for the polymerization of olefins utilizing as a catalyst a metal complex according to claim 12.

14. A process for the polymerization of olefins utilizing as a catalyst a metal complex according to claim 13.

* * * * *